United States Patent [19]

Sawyer

[11] Patent Number: 5,156,613
[45] Date of Patent: Oct. 20, 1992

[54] COLLAGEN WELDING ROD MATERIAL FOR USE IN TISSUE WELDING

[75] Inventor: Philip N. Sawyer, Brooklyn, N.Y.

[73] Assignee: Interface Biomedical Laboratories Corp., Brooklyn, N.Y.

[21] Appl. No.: 654,860

[22] Filed: Feb. 13, 1991

[51] Int. Cl.$^5$ ............................................. A61B 17/00
[52] U.S. Cl. ...................................... 606/213; 606/8; 606/214; 606/40; 128/898
[58] Field of Search .................. 606/213, 214, 215, 3, 606/8, 27; 128/898; 514/801

[56] References Cited

U.S. PATENT DOCUMENTS

| | | | |
|---|---|---|---|
| 3,527,224 | 9/1970 | Rabinowitz | 606/214 |
| 3,742,955 | 7/1973 | Battista | 606/214 |
| 4,122,853 | 10/1978 | Smith | 128/303.1 |
| 4,238,480 | 12/1980 | Sawyer | 424/177 |
| 4,638,800 | 1/1987 | Michel | 606/14 |
| 4,672,969 | 6/1987 | Dew | 606/3 |
| 4,854,320 | 8/1989 | Dew et al. | 606/9 |
| 4,878,492 | 11/1989 | Sinofsky et al. | 128/303.1 |
| 4,929,246 | 5/1990 | Sinofsky | 606/3 |
| 4,930,504 | 6/1990 | Diamantopoulas et al. | 606/3 |
| 5,021,452 | 6/1991 | Labbé et al. | 514/474 |

OTHER PUBLICATIONS

J. Pachence et al., "Collagen: Its Place in the Medrail Device Industry", Jan. 1987.
J. Komerska et al., "Collagen Films as Test Surfaces for Skin-Contact Pressure Adhesives" 1990.
S. Shapiro et al., "Microvascular End-To-Side Arterial Anastomosis Using the Nd:YAG Laser", Neurosurgery, vol. 25, No. 4 (1989) pp. 584-589.
T. Benke et al., "Comparative Study of Suture and Laser-Assisted Anastomoses in Rat Sciatic Nerves", Lasers in Surgery and Medicine, 9:602-615 (1989).
Popp et al., "Welding of Gallbladder Tissue with a Pulsed 2.15 μm Thulium- Holmium - Chromium: YAG Laser", Lasers in Surgery and Medicine, 9:155-159 (1989).
Oz et al., "Tissue Soldering by Use of Indocyanine Green Dye-Enhanced Fibrinogin with the Near Infrared Diode Laser", Journal of Vascular Surgery, vol. 11, No. 5, pp. 718-725 (1990).
Libutti et al., "Canine Colonic Anastomoses Reinforced with Dye-Enhanced Fibrinogen and a Diode Laser", Surgical Endoscopy, vol. 4, No. 2, pp. 97-99 (1990).
Oz et al., "Effects of a 2.15 - Micron Laser on Human Atheroscherotic Xenografts in Vivo", Angiology, The Journal of Vascular Diseases, vol. 41, pp. 772-776 (1990).
Bass et al., "Anastomosis of Biliary Tissue with High--Frequency Electrical Diathermy", Surgical Endoscopy, vol. 4, No. 2, pp. 94-96 (1990).
Oz et al., "A Fiberoptic Compatable Midinfrared Laser with $CO_2$ Laser-Like Effect: Application to Atherosclerosis", Journal of Surgical Research, vol. 17, No. 6, pp. 493-501 (1989).
Oz et al., "Strength of Laser Vascular Fusion: Preliminary Observations on the Role of Thrombus", Lasers in Surgery and Medicine, vol. 10, pp. 393-395 (1990).
Chuck et al., "Dye-Enhanced Laser Tissue Welding", Lasers in Surgery and Medicine, vol. 9, pp. 471-477 (1989).
Oz et al., "In Vitro Comparison of Thulium-Holmium-Chromium: YAG AND Argon Ion Lasers for Welding of Biliary Tissue", Lasers in Surgery and Medicine, vol. 9, pp. 248-253 (1989).
Treat et al., "Preliminary Evaluation of a Pulsed 2.15 μm Laser System for Fiberoptic Endoscopic Surgery", Lasers in Surgery and Medicine, vol. 8, pp. 322-326 (1988).
Bass et al., "Sutureless Microvascular Anastomosis Using the THC: YAG Laser: a Preliminary Report", Microsurgery, vol. 10, pp. 189-193 (1989).

*Primary Examiner*—Stephen C. Pellegrino
*Assistant Examiner*—Gary Jackson
*Attorney, Agent, or Firm*—Pennie & Edmonds

[57] ABSTRACT

A method of joining or reconstructing biological tissue which comprises applying optical energy to the biological tissue while providing a collagen filler material thereto; denaturing the collagen filler material and biological tissue with the optical energy to cause joining of the collagen filler material and biological tissue, thus joining or reconstructing such tissue.

20 Claims, 2 Drawing Sheets

COLLAGEN WELDING ROD MATERIAL FOR USE IN TISSUE WELDING

BACKGROUND OF THE INVENTION

1. Technical Field

The present invention relates to the use of laser emitted optical energy or radio frequency ("RF") energy for joining, repairing or reconstructing biological tissue. In particular, the present invention relates to a method of utilizing a collagen welding rod material in combination with such optical or RF energy as a filler to join, repair or rebuild biological tissue.

2. Background Art

Optical energy, in particular that generated by lasers, has been applied and utilized in the medical field for a variety of surgical purposes. The medical industry initially utilized industrial lasers for the destruction of tumors or surface lesions in patients. At that time, the lasers were relatively crude, high powered and ineffective for delicate internal biological applications.

Subsequently, a variety of cauterization techniques were developed utilizing either laser or RF techniques. Laser optical energy was also utilized to reduce the flow of blood in an open wound or in a surgically created incision: the optical energy being supplied in sufficient quantity to sear or burn the blood vessels thus sealing the open ends of the capillaries and preventing blood flow. A typical use of laser cauterization is described in U.S. Pat. No. 4,122,853. Again, the types of lasers utilized at that time provided very high power application and very high wattage with the surrounding tissue also being destroyed, thus causing longer healing times, infection and scarring.

As newer, lower powered lasers were developed, techniques were developed for atheroma ablation or other endarterectomy procedures for blood vessels. One such procedure is disclosed in U.S. Pat. No. 4,878,492. The $CO_2$, YAG and Excimer lasers all provided substantial improvements in these procedures due to their lower power output. These more sophisticated devices each provide better aiming of a narrower optical energy beam such that destruction of the walls of the blood vessels can be minimized. Also, advances in optical fiber technology allowed the surgeon to conduct more accurately the optical energy to the desired location with greater precision.

Lasers have also been used to "glaze" the internal surfaces of blood vessels after balloon dilation and laser angioplasty in an attempt to prevent medical recollapse, intimal fibroplasia, and reobliteration.

Another procedure which has been developed includes the use of optical energy for welding or otherwise joining or connecting biological tissue. The original attempts to carry out these procedures began in the late 1960's and almost all universally met with failure not so much because of an inability to weld or join the tissue together, but because of the weakness of the resulting weld. The use of the lower powered laser devices, either alone or in combination with physiologic solutions, however, allowed the surgeon to cool the weld site sufficiently to obtain slight improvements in weld strength. Furthermore, RF energy has recently been utilized in both uni- and bi-polar generators to attempt to "weld" or "solder" biological tissue.

U.S. Pat. No. 4,672,969 discloses one method and apparatus for utilizing laser emitted optical energy to effect wound closure or other reconstruction of biological tissue by applying the optical energy to produce thermal heating of the biological tissue to degree suitable for denaturing the tissue proteins such that the collagenous elements of the tissue form a "biological glue" which seals the tissue to effect the joining. This glue is later reabsorbed by the body during the healing process. The patent discloses a number of different types of lasers with preference stated for the Nd:YAG type, because its particular wavelength allows optical energy to propagate without substantial attenuation through water and/or blood for absorption in the tissue to be repaired.

Despite these improvements, however, the weakness of the weld joint still remains as the primary disadvantage of this procedure and extensive current research is being conducted in an attempt to improve on that deficiency. I have now invented a simple yet elegant welding procedure for biological tissue utilizing laser or RF energy which overcomes the shortcomings of the prior art.

SUMMARY OF THE INVENTION

The present invention relates to a method of joining or reconstructing biological tissue which comprises applying optical energy to the biological tissue while providing a collagen filler material thereto; denaturing or melting the collagen filler material and adjacent biological tissue with the optical energy to cause mixing of the denatured or melted collagen filler material and biological tissue, thus joining or reconstructing such tissue. This method may also include adhesively attaching the collagen filler material to the biological tissue to assure proper placement of the filler material adjacent the tissue. This may be achieved by applying the collagen material adjacent the biological tissue with fibrin glue or other biological tissue adhesive.

Often, the biological tissue includes an incision and the method enables the surgeon to enclose the incision by the mixing and joining of the denatured or melted collagen filler material and biological tissue. If desired, spaced sutures may be placed in tissue surrounding the incision to fix the position of adjacent tissue.

The collagen filler material may be prepared by dissolving a predetermined amount of collagen material in water to from a solution, followed by drying or freeze drying of the solution in the desired form and shape of the collagen filler material. Preferably, the collagen material used to prepare the filler material is a mixture of an insoluble collagen material and a soluble collagen material in a weight ratio of about 1:3 to 3:1.

The present method also contemplates applying a physiologically acceptable solution to one of the collagen filler materials or the biological tissue to control the temperature of the joint due to the optical or RF energy imparted thereto. The applied energy is provided by a laser or RF generator having sufficient power dissipation to cause the energy to be absorbed by the tissue and collage filler material. This applied energy is then converted to heat which is within a range bounded by the minimum absorption rate at which the protein elements of the tissue and collagen filler material are converted to melted collagen and by a maximum absorption rate which would cause water in the tissue or collagen filler material to boil. The RF energy provided by uni- or bi-polar techniques also will melt the collagen filler material into the defect or joint area. Thus, the protein elements of the tissue and the collagen filler metal can be melted or denatured, mixed or combined, and then cooled to form a weld joint.

When the biological tissue includes a lesion, the method further comprises forming a seal of collagen material near or upon the lesion. When the lesion comprises at least two separated segments of biological tissue, the method further comprises placing the two segments of tissue in close proximity, and guiding the optical or RF energy and collagen filler material into the area of their junction for joining or reconstruction thereof.

BRIEF DESCRIPTION OF THE DRAWINGS

The features and advantages of the present invention are more readily understood when read in conjunction with the attached drawing figures wherein.

DETAILED DESCRIPTION OF THE PREFERRED EMBODIMENTS

Figure 1:
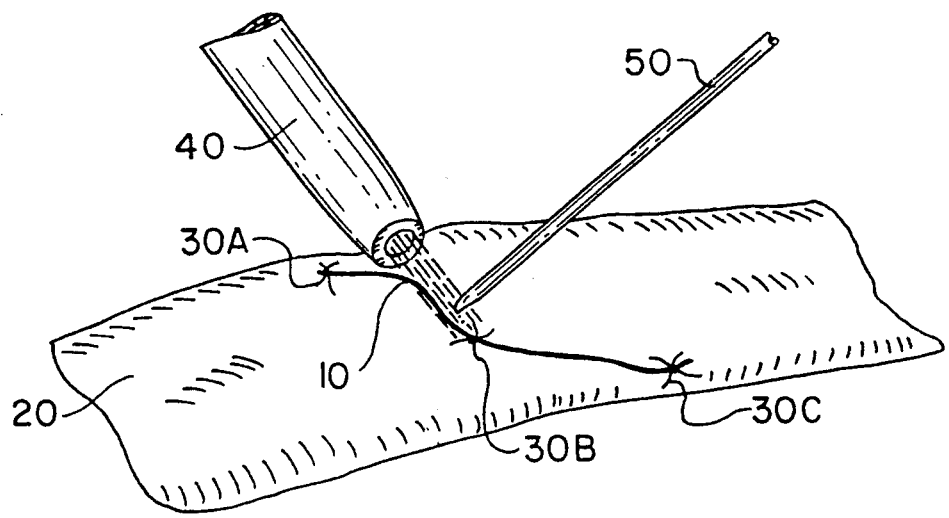
FIG. 1 is a perspective view of the use of a collagen welding rod for closing an incision in a blood vessel with the use of a laser or bipolar RF electrode.

It is well known that biological tissue includes cell layers in a protein framework which provides tensile strength. The proteins are amino acids, and it is known that the application of heat or optical energy can denature such proteins. When the source of heat or energy is removed, the proteins if not totally broken down cool and being to reconfigure and form an approximate replication of the prior tissue structure.

The prior art teaches that the application of either optical energy from a laser or RF energy from a suitable generator could be used to bring the temperature of the biological tissue above room temperature but below the boiling point of water (preferably between 45–75° F. and more preferably 60–70° F). The denaturing of collagen, a major source of protein in the human body, can also be achieved by the application of energy, and is believed go into solution and form a type of "biological glue" which seals the incision or discontinuity in the biological tissue. Thus, it is possible to seal lesions, anastomose a severed or incised vessel or to reconstruct diseased or damaged tissue.

I have found that a major disadvantage of such laser welding procedures for rejoining incised tissue is that insufficient tissue material is present for completing a successful joint. When optical energy from the laser actually denatures or melts the tissue in the areas to be joined, a portion of the tissue thickness is reduced so that the denatured materials can flow towards each other and stick together to form the joint. On relatively thin sections of tissue to be joined, such as in repairing an incised blood vessel wall, there is insufficient denatured material in the joint area for providing a sound, high tensile strength connection.

Collagen is known for use in the medical field as a material for repairing tissue damage caused by thermal, chemical or mechanical trauma (see, e.g., "Collagen: Its Place In the Medical Industry" by J.M. Pachence, et al., Medical Device and Diagnostic Industry, Jan., 1987). I have found that this material can be used as a separate source of collagen for use as filler which can be placed in the path of the laser beam, melted or denatured, and directed into the incision or the tissue which is to be reconstructed. Bi-polar or uni-polar RF energy will also yield the same or substantially similar results. Based on qualitative observations, the additional collagen molecules provided by the filler material allows the tensile strength of the welded incision to be significantly increased.

The application of optical energy and the use of additional collagen material provides several advantages in addition to increased tensile strength. The healing time of the wound is accelerated because blood supply to the affected tissue can be reestablished immediately after the surgical procedure. In addition, little or no scarring is produced because sutures are eliminated or substantially minimized. Furthermore, the various techniques disclosed herein enhance the accuracy of the welding procedure thus avoiding optical or RF energy damage to adjacent or unintended areas of such tissue.

A wide variety of collagen materials may be used as a filler in this laser welding procedure. The most common source may be obtained from bovine hides. Another material which is ideal from the standpoint of melting, flowing, and compatibility with biological tissue is a collagen-like substance which has been modified by dissolving collagen in water and modifying the thusly dissolved collagen to render its surface charge effectively more positive than prior to modification. This material is well known and is disclosed, e.g., in U.S. Pat. No. 4,238,480. The modified collagen is freeze-dried to form a solid mass of gelatin. In accordance with the teachings of the present invention, this mass of gelatin may be formed in the shape of a rod, strip, film or flake and utilized as a filler in a laser welding procedure.

Other forms of collagen which are suitable for use in the present invention include Semed F, a collagen preparation manufactured in native fiber form without any chemical or enzymatic modifications, and Semed S, a lyophilized collagen powder extracted from fresh bovine hides. Each of these products is available from Semex Medical, Frazer, Pa. The Semed F material is a Type I collagen (greater than 95%), while the Semed S is a mixture of Type I and Type III collagen macromolecules in which the shape and dimension of tropocollagen in its natural helical orientation is retained.

Either of the Semed S and Semed F collagen material may be formed into welding filler metal by suspending a suitable amount (usually between about 0.5 and 10 weight percent) of the material in deionized water to form a viscous solution followed by drying the solution under the action of heat or by freeze-drying of the solution, followed by vacuum treating and heating steps. As above with the gelatin material, the final shape of the material can be in the form of a rod, strip, powder, etc. A paste formulation may also be formed by dissolving relatively large amounts of the material in relatively small amounts of saline or deionized water.

The shapes of these formed materials are solid and soft but firm. These materials may be readily sliced or cut to the desired sizes for use in the laser welding procedure. Also, the desired size and shape can be achieved by freeze-drying the material in a suitably sized mold which is configured to the desired size and shape of the product. The thicknesses of the rods or sheets can be between ¼ and 2 mm, depending upon the size of the incision to be joined or area of tissue to be reconstructed. When the paste form is utilized, it may be painted or dropped onto the ares of tissue to be joined or reconstructed. Thus, the surgeon can choose from a wide variety of shapes, sizes, densities, thicknesses and configurations of such filler material depending upon the type of tissue to be welded.

The concentration of the collagen in the liquid which is to be freeze-dried can range from 0.5-10% and preferably 1-5%, with the lower concentrations forming less dense or discontinuous solids. At lower concentrations of 0.5 to 1%, the Semed F forms a structure which approximates dense cobwebs.

Native collagen film, wherein the film strength is preserved and the triple-helix structure of the collagen polymer is maintained intact, can also be used, either alone or with a plasticizer incorporated therewith. A typical collagen sheet is cast from solution to a thickness of about 1.8 to 2 mm and contains the following composition by weight: collagen 70.3%, plasticizer (typically glycerol or glycerine) 16.9%, water 9%, other 3.8%. Such a material is available from Norwood Medical Products Division of Norwood Industries, Inc., Malverne, Pa.

When gelatin or other water soluble forms of collagen are utilized, certain advantages are provided in that the material will readily polymerize at body temperatures to form a stable subcutaneous gel. In addition, when implanted into the body as filler material in the weld joint, the polymerized material will become rapidly populated by host fibroblasts. Thus, the material become vascularized and can remain histologically stable for up to 18 months. One problem with gelatin material, per se however, is that it is highly soluble in blood such that the flow of blood across the material will cause it to dissolve. Thus, gelatin or other soluble collagen material when used along as laser weld filler should be limited to areas where direct contact with blood is avoided or minimized.

It is also possible to use mixtures of the various types of collagen to obtain the most desirable features of each grade. For example a 50/50 mixture of Semed F and strength values of the F grade while retaining the superior flow properties of the S grade. Proportions ranging from 3:1 to 1:3 also form useful mixtures. In addition, the gelatin material described above can be used in combination with the Semed F to achieve similar results.

A wide variety of laser sources may be used to provide the desired optical energy. Typical devices are listed in Tables I and II. Low wattage devices, such as those utilizing argon or $CO_2$, would be the most useful for such welding because of their lower energy output. Higher energy output devices, such as electrostatic and RF frequency coagulators (available from Everest, ValleyLab, or Medtronics) using bipolar tips can also be used to denature or melt the collagen filler materials. Since these devices have greater power input, they can burn the collagen to a greater extent than the argon or $CO_2$ lasers. One skilled in the art, however, is able to control and successfully utilize these higher power devices in accordance with the teachings of the present invention.

Figure 2:
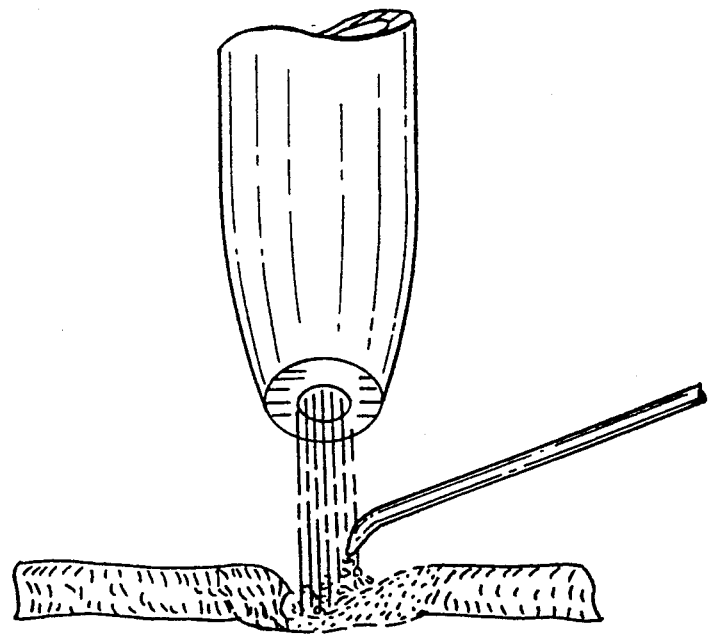
FIG. 2 is a detail of the denatured or melted collagen material in the weld joint of FIG. 1.

The protocol for the process is further appreciated by reference to FIG. 1. An incision 10 in a blood vessel 20 is closed by first applying three approximating sutures 30a, 30b and 30c followed by heating the tissue on either side of the incision with the laser 40. Additional collagen filler material is applied to the incision by placing the tip of welding rod 50 into the laser beam near the heated portion of the incision. The welding rod 50 is literally melted (i.e., denatured) to provide additional collagen which flows onto or over the incision, mixes with the melted or denatured tissue, and thereafter cools and fuses to the underlying tissue substrate. FIG. 2 shows a detail of the joint as it is being made by this procedure.

As noted above, the use of such additional collagen material allows the tensile strength of the joint to be significantly increased over weld joints which do not include additional collagen filler material. This difference in tensile strength is due

TABLE I

| TYPE | WAVELENGTH ($\mu$) | F | ENERGY RANGE/PHOTONS | PENETRATION | COMMENTS |
|---|---|---|---|---|---|
| $CO_2$ | 10.6 | $2.8 \times 10^{13}$ | $3.7 \times 10^{19}$ | microns | low penetration |
| Helium-Neon | .634 | | almost nil | nil | target laser |
| Neodymium - Multiple | 1.06 | $2.8 \times 10^{14}$ | $5.3 \times 10^{18}$ | high | yttrium-aluminum garnet |
| Harmonics Yag | 0.532 | $5.6 \times 10^{14}$ | $2.7 \times 10^{18}$ | Welds tissue at low energy | Increasing penetration increasing |
| | 0.353 | $8.4 \times 10^{14}$ | $1.8 \times 10^{18}$ | | |
| | 0.266 | $1.1 \times 10^{15}$ | $1.3 \times 10^{18}$ | | |
| Argon | 4.8 5.12 | $1.1 \times 10^{14}$ | $3.8 \times 10^{19}$ | 2–400$\mu$ | water absorption |
| Excimer (Excitable dimer) | | | | | |
| Xe CL | .308 | $9.7 \times 10^{14}$ | $1.6 \times 10^{18}$ | <20$\mu$ | very short |
| Xe F | .351 | $8.6 \times 10^{14}$ | $1.8 \times 10^{16}$ | gasifies | operational |
| Kr F | .248 | $1.2 \times 10^{15}$ | $1.3 \times 10^{18}$ | calcified | distance |
| Ar F | .193 | $1.6 \times 10^{15}$ | $9.7 \times 10^{17}$ | plaques | increases safety |

Semed S allows the joint to obtain the higher tensile

TABLE II

| | Proposed Laser-Fiberoptic System | | | | | |
|---|---|---|---|---|---|---|
| Laser | Wavelength NM | Pulse Duration | Principal Fiber | Plaque Ablation | | Operating Range |
| | | | | Efficiency | Calcified | |
| Excimer | 248 | | | H | Y | ? |
| | 308 | 2–200 nsec | Silica | H | Y | L |
| | 351 | | | M-H | Y(?) | L |
| Argon | 488, 512 | 40 msec-CW | Silica | L-M | N | M-H |
| Dye Laser | 450–800 | 1–2 $\mu$sec | Silica | M | ? | M |

TABLE II-continued

| Laser | Wavelength NM | Proposed Laser-Fiberoptic System | | Plaque Ablation | | Operating Range |
| --- | --- | --- | --- | --- | --- | --- |
| | | Pulse Duration | Principal Fiber | Efficiency | Calcified | |
| Nd:YAG | 1,064 | $10^{-9}$–$10^{-12}$ sec | None | H | N(?) | O |
| | | CW | Silica | L | N | M-H |
| Ha:YLF | 2,060 | 100 μsec | Silica | M | ? | M-H(?) |
| Er:YAG | 2,940 | 100 μsec | $ZnF_4$ | H | Y | H |
| $CO_2$ | 10,600 | 1 μsec | Halide(?) | H | Y(?) | ? |
| | | 10 msec | Halide | M-H | N | L |
| | | CW | Halide | L | N | L |

H. indicated high; Y. yes; L. low; M. medium; CW. continuous wave; N. no; Nd. Neodymium; Ha. Hafnium, Er. Erbium
1. indicated extensive thermal damage; 2. strong water absorption; 3. possible mutagenicity; 4. nonthermal active mechanisms; 5. developmental fibers.

to the fact that the collagen filler material provides an additional collagen molecular substrate specifically in the area to be joined. The present technique therefore is analogous to the tungsten inert gas ("TIG") welding of metals such as steel or aluminum. In the TIG process, additional filler metal is almost always used on thin sections. Since the biological tissue to be joined is often relatively thin, similar improvements are obtained when using a collagen filler material than by attempting to make the joint without such filler material.

It has been found that a $CO_2$ or argon laser with a half to one watt power is eminently suitable for making this type of joint. As noted above electrostatic generators can also be used. In addition, an argon electrocoagulator operated at 15-50 volts and 5-20 watts can also be used to denature and melt the collagen welding rod materials and surrounding tissue.

In an attempt to maintain the temperature of the tissue joint at the relatively low value, saline can be used. This is accomplished by dipping the collagen welding rod into saline prior to placing the saline dipped collagen welding rod adjacent to joint area or by dripping saline into the weld. In actual testing, saline cooling makes a different of approximately 23° C. in the joint area (e.g., about 47° C. compared to about 70° C. without saline cooling).

The present invention resolves many of the problems of the prior art. When welding biological tissues, it is difficult to achieve uniformly good results. This problem is due in part to the inability of the surgeon to uniformly melt the biological tissue on each side of the joint to obtain a satisfactory weld. With the use of collagen welding rod as proposed by the present invention, additional collagen material is supplied to the joint from the rod to compensate for any overmelting of tissue on either side of the joint. This also provides an abundance of additional material to seal voids or other defects caused by overheating of tissue. Thus, the reproducibility of the procedure and the attainment of uniform weld joints are significantly improved by the present invention.

All different types of biological tissue may be treated according to the present procedures. For example, all types of blood vessels, including veins, arteries, etc. in the vascular system can be connected or repaired, as can muscle, fascia, tendon, skin or even nerve material.

Figure 3:
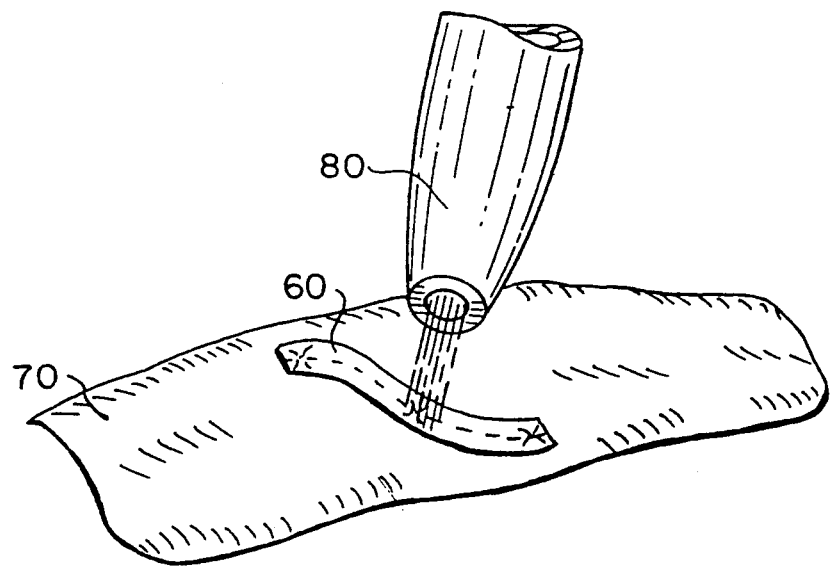
FIG. 3 is a perspective view of the use of a collagen strip in the laser joining of an incision.
Figure 4:
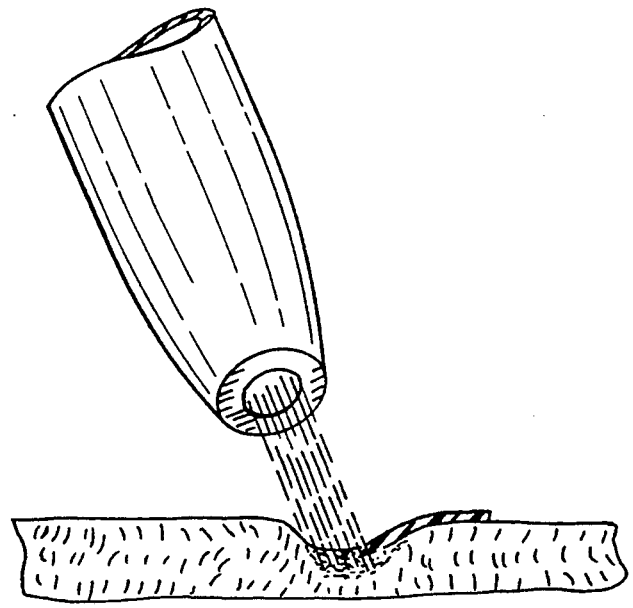
FIG. 4 is a detail of denatured or melted collagen material being applied upon a tissue defect or lesion.

Another procedure in accordance with the present invention is illustrated in FIG. 3. In that FIG., the incision is covered with a flat strip of collagen material 60 along its entire length. The adjacent blood vessel walls 70 on each side of the incision are overlapped by this strip 60 of collagen material. The laser 80 heats the strip of material and the adjacent blood vessel walls 70 to denature those materials into a mass which then solidifies to form the laser welded joint. Again, the use of the strip of collagen material 60 facilitates the welding operation and improves the resultant tensile strength of the weld joint. FIG. 4 shows a detail of the use of the strip material to fill a tissue defect or other lesion.

In an alternate embodiment of the invention, in order to insure that the placement of the welding rod remains in the appropriate position for allowing denatured collagen to flow into the joint area, it is possible to secure or attach the filler metal to the area to be joined. An easy way to accomplish this is to dip the filler material into fibrin glue prior to applying the filler material to the area to be welded. In addition to retaining the filler in the appropriate area desired, the fibrin glue or other biological tissue adhesive also appears to act as a flux which assists in directing the denatured or melted collagen material into the incision.

In yet another embodiment, the procedure can be performed endoscopically: i.e., access to the area desired to be repaired or reconstructed can be made through multiple naturally or surgically created apertures: one aperture is used for insertion of the laser, another for the insertion of the filler material, and a third for monitoring the procedure with an optical fiber connected to an eye-piece or a video camera while the procedure can be visually observed through the eyepiece or camera, the presentation of the procedure on a monitor is preferred because the incision can be viewed in an enlarged mode so that the surgeon can accurately determine the proper placement of the filler material and completion of the joint.

EXAMPLES

The following examples illustrate applications of the welding procedures of the present invention. A dog was anesthetized and its neck and groin area prepared for access. The carotid artery and jugular vein were exposed and clamped, and a one inch incision was made in each one. An argon laser operated at about one-half watt was used to reweld the clamped joints with one of Semed S, Semed F, and modified collagen material (i.e., gelatin) as described above. Sutures were included at each end of the incision to prevent propagation of the incision during the welding operation.

The gelatin samples welded beautifully in that they readily melted, and simply and easily filled incision and rapidly formed a solid weld joint. However, upon exposure to blood, this material was solubilized by the blood which broke through the weld due to dissolution. The Semed F samples did not flow as readily into the joint, but once the joint was made, a very high tensile strength repair was obtained. The performance of the Semed S was intermediate between the modified polymer and Semed F both with respect to joint strength and fluidity. Mixtures of either Semed S or modified collagen (gelatin) with the Semed F material, in a 50/50 ratio provides the benefits of each material are achieved in a single filler rod material.

Both bi-polar and uni-polar RF electrodes were also utilized to denature or melt various samples of modified gelatin, Semed F and Semed S, both alone and in combination, into arteriotomies and venotomies. A vascular anastomosis was also crated using Semed F in accordance with the above-described welding technique. The weld joint was observed to be of high tensile strength. In addition, initial attempts at approximating muscle tendon and skin have been successfully completed.

While it is apparent that the invention herein disclosed is well calculated to fulfill the objects above stated, it will be appreciated that numerous embodiments and modifications may be devised by those skilled in the art and it is intended that the appended claims cover all such modifications and embodiments as fall within the true spirit and scope of the present invention.

What is claimed is:

1. A method of joining or reconstructing biological tissue which comprises applying optical or RF energy to the biological tissue while providing a collagen filler material thereto; denaturing or melting the collagen filler material and adjacent biological tissue with the applied energy to cause mixing of the denatured or melted collagen filler material and biological tissue, thus joining or reconstructing such tissue.

2. The method of claim 1 which further comprises adhesively attaching the collagen filler material to the biological tissue to assure proper placement thereof.

3. The method of claim 1 wherein the biological tissue includes an incision and which further comprises enclosing said incision by the mixing and joining of the denatured or melted collagen filler material and biological tissue.

4. The method of claim 3 which further comprises placing spaced sutures in tissue surrounding said incision to fix the position of adjacent tissue.

5. The method of claim 1 which further comprises applying said collagen material adjacent said biological tissue with fibrin glue.

6. The method of claim 1 which further comprises preparing said collagen material by dissolving a predetermined amount of collagen material in water to form a solution, followed by drying of the solution in the desired form and shape of said collagen filler material.

7. The method of claim 1 wherein the collagen material used to prepare the filler material is a mixture of an insoluble collagen material and a soluble collagen material.

8. The method of claim 7 wherein the weight ratio of the soluble collagen to the insoluble collagen is between about 1:3 to 3:1.

9. The method of claim 1 which further comprises applying a physiologically acceptable solution to one of the collagen filler material or the biological tissue to control the temperature of the joint due to the optical energy imparted thereto.

10. The method of claim 1 wherein the applied energy is provided by a laser or RF generator having a power dissipation sufficient to cause the energy to be absorbed by the tissue and the collagen filler material and converted to heat and to be within a range bounded by a minimum absorption rate at which the tissue and collagen filler material are converted to a denatured or melted collagen and by a maximum absorption rate at which water in the tissue or collagen filler material would boil, such that protein elements of the tissue and the collagen filler metal can be denatured or melted, mixed or combined and cooled to form a weld joint.

11. The method of claim 1 wherein the biological tissue includes a lesion and wherein the method further comprises forming a seal of collagen material near or upon said lesion.

12. The method of claim 11 wherein the lesion comprises at least two separated segments of biological tissue and the method further comprises placing said two segments of tissue in close proximity, and guiding said optical energy and filler material into the area of their junction.

13. A method of joining or reconstructing biological tissue which comprises applying optical or RF energy to the biological tissue while providing a collagen filler material thereto; applying a biological tissue adhesive to retain the collagen filler material in a desired location with respect to the tissue; denaturing or melting the collagen filler material and adjacent biological tissue with the applied energy to cause mixing of the collagen filler material and biological tissue, thus joining or reconstructing such tissue.

14. The method of claim 13 wherein the biological tissue includes an incision and which further comprises enclosing said incision by the mixing and joining of the denatured or melted collagen filler material and biological tissue.

15. The method of claim 14 which further comprises placing spaced sutures in tissue surrounding said incision to fix the position of adjacent tissue.

16. The method of claim 13 wherein said collagen material is retained in the desired location by the use of fibrin glue.

17. The method of claim 13 which further comprises preparing said collagen material by dissolving a predetermined amount of collagen material in water to form a solution, followed by drying of the solution in the desired form and shape of said collagen filler material.

18. The method of claim 17 wherein the collagen used to prepare the filler material is a mixture of an insoluble collagen material and a soluble collagen material in a weight ratio of between about 1:3 to 3:1.

19. The method of claim 13 which further comprises applying a physiologically acceptable solution to one of the collagen filler material or the biological tissue to control the temperature of the joint due to the optical energy imparted thereto.

20. The method of claim 13 wherein the applied energy is provided by a laser or RF generator having sufficient power dissipation to cause the energy to be absorbed by the tissue and the collagen filler material and converted to heat and to be within a range bounded by a minimum absorption rate at which the tissue and collagen filler material are converted to a denatured or melted collagen and by a maximum absorption rate at which water in the tissue or collagen filler material would boil, such that protein elements of the tissue and the collagen filler metal can be denatured or melted, mixed or combined and cooled to form a weld joint.

* * * * *